United States Patent [19]

Shannon et al.

[11] 4,309,654

[45] Jan. 5, 1982

[54] METHOD AND APPARATUS FOR TESTING MOISTURE CONTENT OF PULP INSULATION DURING APPLICATION ONTO AN ELECTRICAL CONDUCTOR

[75] Inventors: Michael A. Shannon, Verdun; William E. Cowley, Montreal, both of Canada

[73] Assignee: Northern Telecom Limited, Montreal, Canada

[21] Appl. No.: 83,113

[22] Filed: Oct. 9, 1979

[51] Int. Cl.³ ............................................. G01N 27/12
[52] U.S. Cl. .................................. 324/65 R; 324/54; 425/135
[58] Field of Search .............. 324/54, 65 R; 118/712; 425/135, 169

[56] References Cited

U.S. PATENT DOCUMENTS

| | | | |
|---|---|---|---|
| 2,916,697 | 12/1959 | Boode | 324/54 |
| 3,047,799 | 7/1962 | Peer et al. | 324/54 |
| 3,277,364 | 10/1966 | Abrahamson | 324/54 |
| 3,323,701 | 6/1967 | Gurski et al. | 324/54 |
| 3,413,541 | 11/1968 | Swim et al. | 324/54 |
| 3,546,581 | 12/1970 | Herrendeen et al. | 324/54 |
| 3,555,413 | 1/1971 | Matsuba | 324/54 |
| 4,027,238 | 5/1977 | Loch | 324/65 R |

*Primary Examiner*—Gerard R. Strecker

[57] ABSTRACT

A method and apparatus for testing the moisture content of pulp insulation on an electrical conductor during the application of the insulation onto the conductor, in which first and second potentials are applied across a pair of voltage dividers having the insulation connected in parallel with each divider at its node, obtaining a measure of the potential at each node, and obtaining the difference between the two measures.

10 Claims, 2 Drawing Figures

METHOD AND APPARATUS FOR TESTING MOISTURE CONTENT OF PULP INSULATION DURING APPLICATION ONTO AN ELECTRICAL CONDUCTOR

FIELD OF THE INVENTION

This invention relates to pulp insulated electrical conductors and more particularly to the measurement and control of moisture in continuously coated wire conductors passing from a drying oven.

BACKGROUND OF THE INVENTION

It is important to control the moisture content of pulp insulated electrical conductors because if the pulp insulation is too wet it will deform during later handling and operation of the conductor and if it is too dry the insulation will flake. Also the electrical insulation resistance of the pulp varies in relation to the moisture content. The moisture content is dependent upon the heat of the oven which dries the pulp on the conductor and it may be altered subsequently by heating the conductors which have been made into cable form and wound onto a take-up reel.

In a conventional procedure the moisture content of the pulp is tested after the insulated conductor is wound on the take-up reel subsequent to leaving the drying oven. This is done by severing a sample length of the wound conductor, weighing the sample, heating the sample and weighing it again. In such a procedure a wide range of values must be tolerated if the moisture content varies throughout the length of the wound conductor. Also the delay occasioned by the procedure and the atmospheric moisture content may affect the test results.

To avoid the above-mentioned drawbacks it would be advantageous to test the moisture content of pulp insulation on electrical conductors during the process of applying the insulation but any electrical test which has been formulated has proven unsatisfactory because of the presence of stray charges on the pulp which makes the readings of the test unpredictable. By stray charges we mean all voltages due to static charges, induced electromotive forces and thermoelectric voltages.

It is an object of the present invention to provide an improved method of testing the moisture content of pulp insulation on an electrical conductor during the application of the insulation onto the conductor.

It is a further object of the invention to provide an improved apparatus for testing the moisture content of pulp insulation on an electrical conductor during the application of the insulation onto the conductor.

SUMMARY OF THE INVENTION

In its broadest aspect the invention consists of a method of testing the moisture content of pulp insulation on an electrical conductor during the application of the insulation onto the conductor, comprising the steps of: applying a first potential difference across a first voltage divider comprising two first resistances connected in series through a first node, the insulation on the conductor being connected in parallel with one of the two first resistances, and obtaining a measure of the potential at the first node; applying a second potential difference across a voltage divider comprising two second resistances connected in series through a second node, the insulation on the conductor being connected in parallel with one of the two second resistances, and obtaining a measure of the potential at the second node; said first potential difference and said first two resistances being selected relative to said second potential difference and said second two resistances whereby the components due to the stray charges present in said measures approximately cancel out; and obtaining the difference between the two measures.

The invention also resides in a device for testing the moisture content of pulp insulation on an electrical conductor during the process of applying the insulation to the conductor, comprising: a first voltage divider comprising two first resistances connected in series through a first node, the insulation on the conductor being connected in parallel with one of the two first resistances, and means for applying a first potential difference across the first voltage divider; a second voltage divider comprising two second resistances connected in series through a second node, the insulation on the conductor being connected in parallel with one of the two second resistances, and means for applying a second potential difference across the second voltage divider; and means for obtaining a measure of the potential at the first node and a measure of the potential difference at the second node; said first potential and said first two resistances being selected relative to said second potential difference and said second two resistances whereby the components due to the stray charges present in said measures approximately cancel out; and means to obtain the difference between the two measures.

BRIEF DESCRIPTION OF THE DRAWINGS

An example embodiment of the invention is shown in the accompanying drawings in which.

DETAILED DESCRIPTION OF THE DRAWINGS

Figure 1:
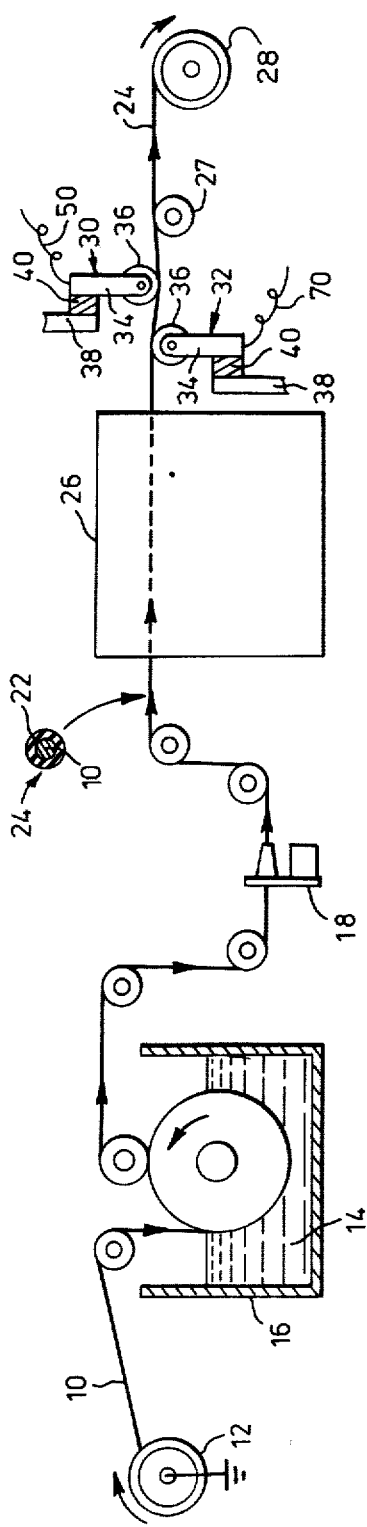
FIG. 1 is a schematic flow diagram showing the continuous application on pulp insulation to an electrical conductor and the testing of the moisture content of the insulation as the conductor leaves the drying oven.
Figure 2:
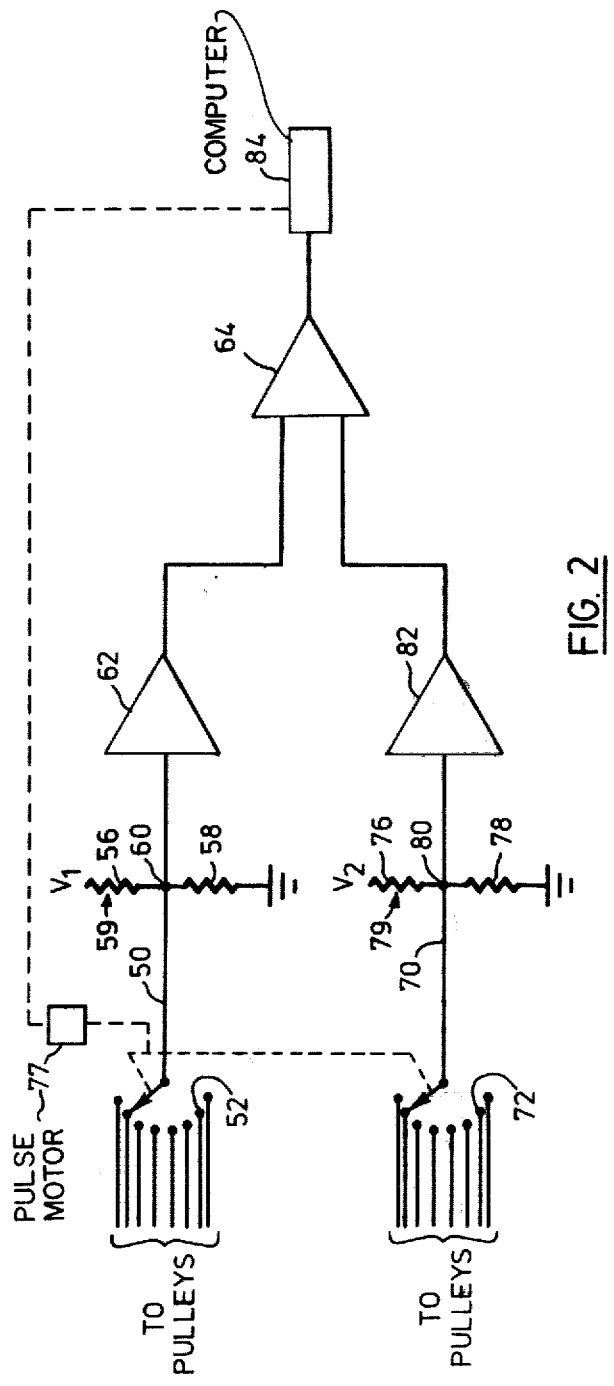
FIG. 2 is a diagram of the electrical circuit associated with the moisture testing apparatus of FIG. 1.

In the production of insulated electrical conductors, as seen in FIG. 1 of the drawings, a bare wire conductor 10 is drawn from a reel 12 and passed through a pulp slurry 14 of insulating fibres in a vat 16 where it picks up a mat of the fibres. Matted wire conductor 10 then passes through a polisher 18 which distributes the fibres uniformly around the wire conductor as a coating of wet pulp insulation 22 to form an insulated conductor 24. Insulated conductor 24 is then passed through an oven 26 to reduce the moisture content of wet pulp coating 22 to about 5% by weight, after which the insulated conductor is passed over a guide roller 27 and wound on a take-up reel 28 for transportation and storage where it may be further dried if desired after twisting and stranding into cable form.

In the example embodiment of the invention shown in the drawings a pair of conducting pulleys 30, 32 are located between oven 26 and take-up reel 28, each pulley contacting insulated conductor 24 after it emerges from the oven. Pulleys 30, 32 are in opposed relationship, pulley 30 (here called the upper pulley) also being offset along insulated conductor 24 from pulley 32 (here called the lower pulley). Each pulley 30, 32 comprises an arm 34 and a circumferentially grooved pulley wheel 36 freely rotatable on the arm. Both pulleys 30, 32 are mounted on a frame 38 which is preferably movable to withdraw the pulleys from the path of insulated conductor 24 when not in use. Arm 34 and pulley wheel 36 are electrically insulated from frame 38 by mounting blocks 40. Pulleys 30, 32 are positioned with respect to each other and to guide roller 27 to provide an arcuate length of contact of insulated conductor 24 with each pulley wheel 36.

A first voltage source $V_1$ is connected to upper pulley 30 through a resistance 56 forming a series circuit comprising resistance 56, step switch 52, pulley 30 and insulation material 22 to grounded wire conductor 10. A grounded resistance 58 is connected in parallel with step switch 52 and upper pulley 34 at a node 60. Resistances 56 and 58 provide a first voltage divider 59. Node 60 is connected to the input of a high impedance amplifier 62 and the output of amplifier 62 is connected to an input of a differential amplifier 64.

Lower pulley 32 is connected by an insulated line 70, in series with a further step switch 72 and a resistance 76, to a second voltage source $V_2$ with insulated conductor 24 as ground. Step switches 52 and 72 are ganged and driven by a pulse motor 77. A grounded resistance 78 is connected in parallel with step switch 72 and lower pulley 36 at a node 80. Resistances 76 and 78 provide a second voltage divider 79. Node 80 is connected to the input of a second high impedance amplifier 82 and the output of amplifier 82 is connected to an input of differential amplifier 64. The output of differential amplifier 64 is connected to a computer 84 which is connected to pulse motor 77.

Lines 50 and 70 are preferably insulated with Teflon (a trade mark). Arms 34 and wheels 36 of pulleys 30, 32 are preferably made of aluminum. Biasing and grounding connections for amplifiers 62 and 82 are omitted for clarity. A suitable high impedance amplifier for use with the invention is model TIL80 manufactured by Texas Instruments Inc. and a suitable differential amplifier for such use is model LM741 manufactured by National Semiconductor Corp.

In the operation of the example embodiment a constant voltage $V_1$ is supplied to upper pulley 36 and the potential at node 60 is measured. The resistance of insulation 22 varies with its moisture content and the current leakage, and hence the voltage, will vary inversely to that resistance. The value of resistance 58 is chosen to approximate the resistance of insulation 22.

Lower pulley 32 also has a constant voltage $V_2$ supplied to it but of a different value, to produce a different measure fed into amplifier 82 although varying in the same manner as the measure fed into amplifier 62. By feeding both measures through differential amplifier 64 a value is obtained which is the difference between the two readings and which is directly proportional to the amount of moisture in the pulp insulation. The subtraction implicit in the operation of the differential amplifier cancels out the stray voltages on insulation 22 of wire conductor 10 which would distort a single readout.

The output from differential amplifier 64 may be read directly or it may be fed into computer 84 which controls ganged step switches 52 and 72 by means of pulse motor 77 to move the switches sequentially through lines 50 connected to a plurality of pulleys 30, 32 measuring the moisture content of an array of insulated conductors 24. Computer 84 may be programmed to allow the components of the circuits to stabilize, then to take a plurality of sequential readings of a single insulated conductor, and finally move step switches 52 and 72 to test the next conductor in the array. By obtaining an average moisture value over a selected period of time, the electrical polarization effects in the components are eliminated.

The output value of differential amplifier 64 will be proportional to the difference between test voltages $V_1$ and $V_2$. In a specific example the applied voltages $V_1$ and $V_2$ were 50 volts and 25 volts respectively. The value of each resistance 56 and 75 was $5 \times 10^9$ ohms while the value of each resistance 58 and 78 was $2 \times 10^9$ ohms.

The lateral deflection of insulated conductor 24 caused by pulleys 30 and 32 should be as small as possible to reduce deformation on insulation 22. On the other hand the length of contact of the conductor with the pulley wheels 36 should be as large as possible since a point contact gives an inordinately high electrical resistance in the insulation to obtain the best test results. The length of contact chosen will reflect a balance between these two considerations.

We claim:

1. A method of testing the moisture content of pulp insulation on a grounded electrical conductor during the application of the insulation onto the conductor, comprising the steps of:

applying a first d.c. potential difference across a first voltage divider comprising two first resistances connected in series through a first node, one end of said first voltage divider being grounded, the outer surface of the insulation on the conductor being directly contacted by a first contact means connected to said first node to connect said insulation in parallel with one of the two first resistances, and obtaining a measure of the potential at the first node;

applying a second d.c. potential difference across a second voltage divider comprising two second resistances connected in series through a second node, one end of said second voltage divider being grounded, the outer surface of the insulation on the conductor being directly contacted by a second contact means connected to said second node to connect said insulation in parallel with one of the two second resistances, and obtaining a measure of the potential at the second node;

said first potential difference and said first two resistances being selected relative to said second potential difference and said second two resistances whereby the components due to the stray charges present in said measures approximately cancel out; and obtaining the difference between the two measures, said difference being directly proportional to the amount of moisture in the pulp insulation.

2. A method as claimed in claim 1 in which the first and second applied potentials are of different value.

3. A method as claimed in claim 1 in which the first and second potentials are applied through electrical contacts which each contact the insulation each along a length thereof.

4. A method as claimed in claim 1 in which the first and second potentials are applied in staggered relationship along the conductor.

5. Apparatus for testing the moisture content of pulp insulation on a grounded electrical conductor during the application of the insulation onto the conductor, comprising:

a first voltage divider comprising two first resistances connected in series through a first node, one end of said first voltage divider being grounded; first contact means connected to said first node and directly contacting the outer surface of the insulation on the conductor to connect said insulation in parallel with one of the two first resistances; and means for applying a first d.c. potential difference across the first voltage divider;

a second voltage divider comprising two second resistances connected in series through a second node, one end of said second voltage divider being grounded; second contact means connected to said second node and directly contacting the outer surface of the insulation on the conductor to connect said insulation in parallel with one of the two second resistances; and means for applying a second d.c. potential difference across the second voltage divider; and means for obtaining a measure of the potential at the first node and a measure of the potential at the second node;

said first potential difference and said first two resistances being selected relative to said second potential difference and said second two resistances whereby the components due to the stray charges present in said measures approximately cancel out; and means to obtain the difference between the two measures, said difference being directly proportional to the amount of moisture in the pulp insulation.

6. Apparatus as claimed in claim 5 in which the first and second applied potentials are of different value.

7. Apparatus as claimed in claim 5 in which said contact means comprises a pair of conducting pulleys, each insulated from ground, contacting the conductor insulation each on an opposite side thereof, each pulley being connected in series with the insulation as part of the one of said parallel connections.

8. Apparatus as claimed in claim 7 in which the pulleys contact the conductor insulation in staggered relationship therealong.

9. Apparatus as claimed in claim 5 in which said means for obtaining a measure of each of the node potentials in a high impedance amplifier.

10. Apparatus as claimed in claim 9 in which the outputs of both high impedance amplifiers are connected to the respective inputs of a differential amplifier.

* * * * *